United States Patent
Giannozzi et al.

(10) Patent No.: US 9,665,771 B2
(45) Date of Patent: May 30, 2017

(54) METHOD AND APPARATUS FOR MEASURING ABERRATIONS OF AN OCULAR OPTICAL SYSTEM

(71) Applicant: Costruzioni Strumenti Oftalmici C.S.O. S.r.l., Scandicci (Florence) (IT)

(72) Inventors: Franco Giannozzi, Scandicci (IT); Francesco Versaci, Prato (IT); Gabriele Vestri, Florence (IT)

(73) Assignee: COSTRUZIONI STRUMENTI OFTALMICI C.S.O. S.R.L., Scandicci (Florence) (IT)

( * ) Notice: Subject to any disclaimer, the term of this patent is extended or adjusted under 35 U.S.C. 154(b) by 144 days.

(21) Appl. No.: 14/439,863

(22) PCT Filed: Nov. 6, 2013

(86) PCT No.: PCT/IB2013/059935
§ 371 (c)(1),
(2) Date: Apr. 30, 2015

(87) PCT Pub. No.: WO2014/111759
PCT Pub. Date: Jul. 24, 2014

(65) Prior Publication Data
US 2015/0294134 A1 Oct. 15, 2015

(30) Foreign Application Priority Data

Nov. 7, 2012 (IT) ................ FI2012A0240

(51) Int. Cl.
*G06K 9/00* (2006.01)
*A61B 3/10* (2006.01)
(Continued)

(52) U.S. Cl.
CPC ............ *G06K 9/0061* (2013.01); *A61B 3/103* (2013.01); *A61B 3/1015* (2013.01);
(Continued)

(58) Field of Classification Search
CPC ............ G06K 9/0061; G06K 9/00604; G06K 9/4661; G06K 9/52; A61B 3/103; A61B 3/1015
See application file for complete search history.

(56) References Cited

U.S. PATENT DOCUMENTS 5,287,165 A 2/1994 Ulich et al.
2004/0257530 A1 12/2004 Chernyak et al.
(Continued)

FOREIGN PATENT DOCUMENTS

| EP | 2063260 A1 | 5/2009 |
|----|-----------|--------|
| EP | 2353736 A1 | 8/2011 |
| WO | 2004025352 A1 | 3/2004 |

OTHER PUBLICATIONS

Wikipedia, "Euler method", Mar. 8, 2012, Wikipedia.org, <https://web.archive.org/web/20120308213631/http://en.wikipedia.org/wiki/Euler_method>, p. 1-7.*
(Continued)

*Primary Examiner* — Chan Park
*Assistant Examiner* — Timothy Choi
(74) *Attorney, Agent, or Firm* — Lucas & Mercanti, LLP

(57) ABSTRACT

The present invention refers in general to the measurement of aberrations of the optical system (E) of a living being, in particular human. More specifically, the invention refers to methods and systems for reconstructing a wavefront (W(z, p)) and/or for constructing a refracting error map.

9 Claims, 9 Drawing Sheets

(51) Int. Cl.
*A61B 3/103* (2006.01)
*G06K 9/46* (2006.01)
*G06K 9/52* (2006.01)

(52) U.S. Cl.
CPC ....... *G06K 9/00604* (2013.01); *G06K 9/4661* (2013.01); *G06K 9/52* (2013.01)

(56) References Cited

U.S. PATENT DOCUMENTS

| 2006/0170868 A1 | 8/2006 | Molebny et al. |
| 2010/0110379 A1* | 5/2010 | Zhou ........................ G01J 9/00 351/211 |

OTHER PUBLICATIONS

International Search Report dated May 23, 2014 for PCT/IB2013/059935.
S.R. Chamot, et al; Adaptive optics for ophthalmic applications using a pyramid wavefront sensor; Optics Express; vol. 14; No. 2; Jan. 2006; XP055070801; pp. 518-526.
A. Burvall, et al; Linearity of the pyramid wavefront sensor; Optics Express; vol. 14; No. 25; Jan. 2006; XP055071229; pp. 11925-11934.

* cited by examiner

FIG. 7

METHOD AND APPARATUS FOR MEASURING ABERRATIONS OF AN OCULAR OPTICAL SYSTEM

CROSS-REFERENCE TO RELATED APPLICATIONS

This application is a 371 of PCT/IB2013/059935, filed Nov. 6, 2013 which, in turn, claimed the priority of Italian Patent Application No. FI2012A000240 filed on Nov. 7, 2012, both applications are incorporated herein by reference.

TECHNICAL FIELD OF THE INVENTION

The present invention refers in general to the measurement of aberrations of the optical system of a living being, in particular a human being.

More specifically, the invention refers to methods and systems for reconstructing a wavefront and/or for constructing a refracting error or defect map.

The measurement of the wavefront of the eye can be used to create an aberration map or elevation map of the wavefront that makes it possible to evaluate aberrations along the entire optical pathway of the eye, comprising both internal aberrations and the aberrations of the corneal surface. The aberrometric map can thus be used to calculate a surgical ablation pattern for a laser system or to design contact lenses to correct complex aberrations in the eye of the patient.

The refracting error map is easier to understand than a wavefront map for anybody not highly proficient in mathematical models, for example for medical staff. It clearly shows the local progression of the vergence error of the optical system observed and thus of its defects (astigmatism, spherical aberration, coma, etc.).

BACKGROUND OF THE INVENTION

The methods currently known for calculating a personalized ablation pattern, which use data coming from wavefront sensors, generally involve mathematical modelling of the optical surface of the eye through series development techniques. More specifically, in order to model the ocular surface polynomials of Zernike polynomials have been used, as proposed by Liang et al., in "Objective Measurement of Wave Aberrations of the Human Eye with the Use of a Harman-Shack Wave-front Sensor", Journal Optical Society of America, July 1994, vol. 11, No. 7, pp. 1-9, the content of which should be considered entirely incorporated here for reference. The coefficients of the Zernike polynomials are derived from well-known fitting techniques, and the refractive correction procedure is thus determined using the shape of the ocular surface of the eye, as indicated by the mathematical model of the series development.

The methods for reconstructing the surface based on Zernike functions and their accuracy in the case of normal eyes have been studied extensively for regular cornea shapes. See, for example, Schweigerling, J., and Grievenkamp, J. E., "Using corneal height maps and polynomial decomposition to determine corneal aberrations," Opt. Vis. Sci., Vol. 74, No. 11 (1997) and Gurao, A. and Artal, P., "Corneal wave aberration from videokeratography: Accuracy and limitations of the procedure," JOSAA, Vol. 17, No. 6 (2000).

Moreover, known modelling techniques are quite indirect, and can lead to unwanted errors in the calculation, as well as a lack of understanding of the physical correction to be made.

Therefore, in light of the above, it is clear that there is a need to be able to have improved methods and systems for mathematically modelling a wavefront.

SUMMARY OF THE INVENTION

The object of the present invention is therefore to overcome the problems outlined above and this is obtained through a method for reconstructing the wavefront as defined by claim 1.

A further object of the present invention is an apparatus as defined in claim 6.

The present invention, by overcoming the problems of the prior art, offers numerous and clear advantages.

In particular, the present invention provides for a specific system described hereafter, software, and methods for measuring and reconstructing an elevation map of the wavefront in an optical system using direct integration algorithms.

This makes it possible to obtain particular advantages with respect to the aforementioned classic methods.

In particular, it makes real time processing possible thanks to the reduced computing complexity, also in the presence of a large number of samples measured.

Moreover, the method proposed can also be used on irregularly shaped pupils, and thus ones that are not circular like those required for example by Zernike fitting in which the functions are defined on a circle.

Moreover, it allows better detection capability of the details, or in other words, better tracking of the progression of the normals. Indeed, the method proposed adapts locally to the progression of the normals instead of adapting globally to their approximation.

Moreover, the present invention makes it possible to determine areas of opacity in the pupil that do not participate in the formation of the image on the retina, due to opacity of the ocular optical means, in particular of the crystalline lens and cornea.

Moreover, the present invention, among other things, makes it possible to also obtain a refractive power map extending to the entire entrance pupil of the patient.

The present invention certainly has an application in an intraoperation tool that can be used during refractive surgical interventions or on those for cataracts.

In the first type of interventions, it may be useful for the practitioner to have real time control of the aberrations of the eye during the procedure for removing the corneal tissue.

In the second type of interventions, when a torus lens is implanted to correct an astigmatism of substantial size, it is extremely useful to have a tool capable of measuring the residual defect during the course of implantation so as to be able to finely optimize the orientation of the implanted lens. If a torus lens is not implanted, on the other hand, the measurement in real time of the cylinder constitutes an effective guide for making limbal incisions (LRI Limbal Relaxing Incision).

BRIEF DESCRIPTION OF THE DRAWINGS

These and other advantages, together with the characteristics and the modes of use of the present invention, will become apparent from the following detailed description of its preferred embodiments, presented as examples and not for limiting purposes. Reference will now be made to the figures of the attached drawings, in which:

FIG. 7 represents a calculation grid for the direct integration method;

DETAILED DESCRIPTION OF PREFERRED EMBODIMENTS

Antefacts of the Invention

For a few years now aberrometers have been present on the market and have been used as devices for objectively measuring the sight defects of a patient: such defects are commonly called aberrations. The derivation of these is obtained from the measurement of the wavefront coming out from the eye coming from a pointed light source positioned on the fovea. With the term "wavefront" it is here meant the equal-phase surface of the light wave coming out from the eye.

In general, an aberrometer is made up of:

a fixation system a frontal observation system of the eye a projection system of a light source onto the retina a system for capturing the wavefront a sensor for measuring the wavefront During an aberrometry examination the patient is asked to stare at a point of light inside the instrument in order to align his visual axis with that of the instrument. The fixation system gives the patient an indication of the correct direction in which to rotate the eye. This system consists of an illuminator and a target, usually a structured one. They are mounted on a mobile slider and can be translated so as to allow the compensation of the spherical defect of the patient.

Figure 1:
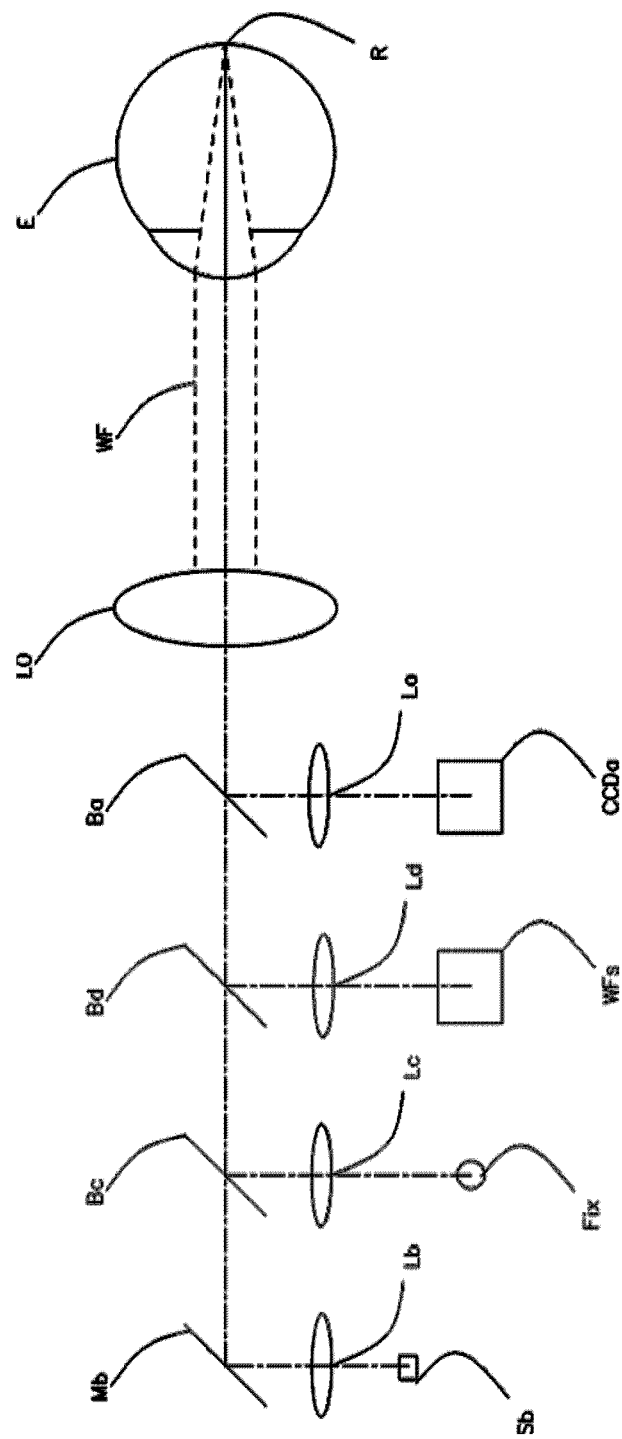
FIG. 1 is a schematization of an aberrometer.

With reference to FIG. 1, in order to correctly align the patient's gaze, the fixation system Fix is made visible to the patient through the optical system Lc, the beam splitter Bc and the frontal lens L0.

The frontal observation system is used by the operator to correctly frame of the patient's eye and to check that he is staring correctly. A capturing system CCDa captures the image of the eye through the optical systems La and L0 and the beam splitter Ba in order to allow the operator to easily align the axis of the instrument at the center of the pupil.

In order to obtain an adequate light source on the retina, a light beam is projected onto the retina through the ocular means (cornea, aqueous humor, crystalline lens, vitreous humor). A fraction of the light that reaches the retina is diffused back by the retina itself and follows the same path back in the opposite direction to how it came in to generate the wavefront emitted by the eye. The light emitted by a source Sb (usually a low power laser) passing through the optical system Lb, is reflected by the mirror Mb passing through the frontal lens L0, enters into the patient's eye and, through his pupil, generates a point of light on the retina R of the patient.

Figure 2:
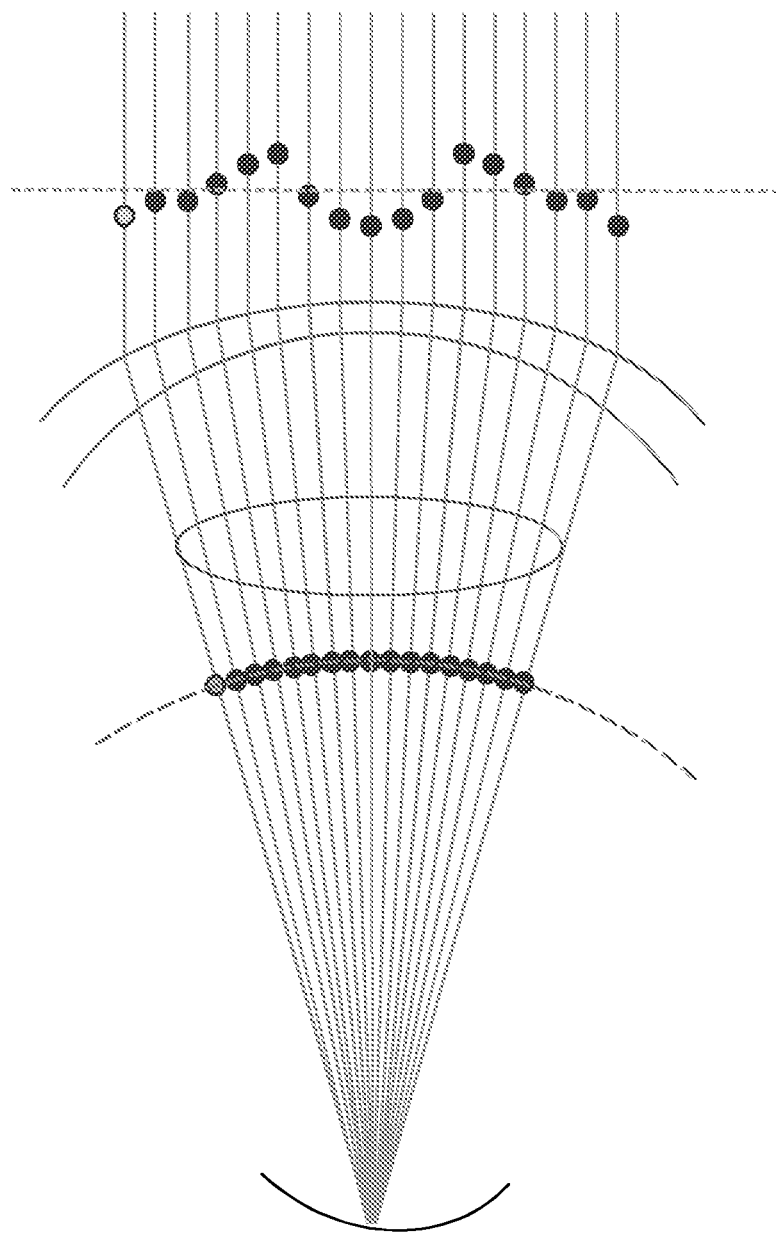
FIG. 2 is an example representation of a wavefront.

In an ideal eye the re-emitted wavefront is flat. In a real eye the aberrations distort the ideal profile into more complex shapes (see for example FIG. 2). From a reconstruction of the shape of the re-emitted wavefront it is possible to obtain information on the performance of the ocular system under examination.

An aberrometer device captures the output pupil of the eye and creates an image thereof inside it to measure its wavefront with a suitable sensor.

Again with reference to FIG. 1, a capturing system containing the optical systems L0 and Ld and the beam splitter Bd transfers the wavefront, of which the aberrations are to be measured, to the generic wavefront sensor WFs.

In literature, various devices for measuring a wavefront are known: among them the most common in ophthalmology is the Hartmann-Shack sensor (HSS).

This, positioned at the image of the output pupil of the eye, makes it possible to measure the partial derivatives in x and y of the wavefront in roughly a thousand points distributed over a pupil of about 9 mm in diameter.

It is made up of an array of micro-lenses that split the incident wavefront into smaller locally "flat" wavefronts that are focused on a suitable sensor. A local slope of the wavefront under examination determines a derivation of the point focused by a micro-lens from a predetermined typical position of a non-aberrated wavefront.

An ideal wavefront, characterised by normals that are anywhere parallel to the same direction, will produce a regular grid of evenly spaced image points.

An aberrated wavefront, in which the normals are not parallel to one another, will produce a more or less disorderly and irregular grid of image points on the sensor. The deviation of the position of the image points from that of the points of a calibration grid makes it possible to calculate the gradient of the wavefront or rather its partial derivatives in x and y.

Figure 3:
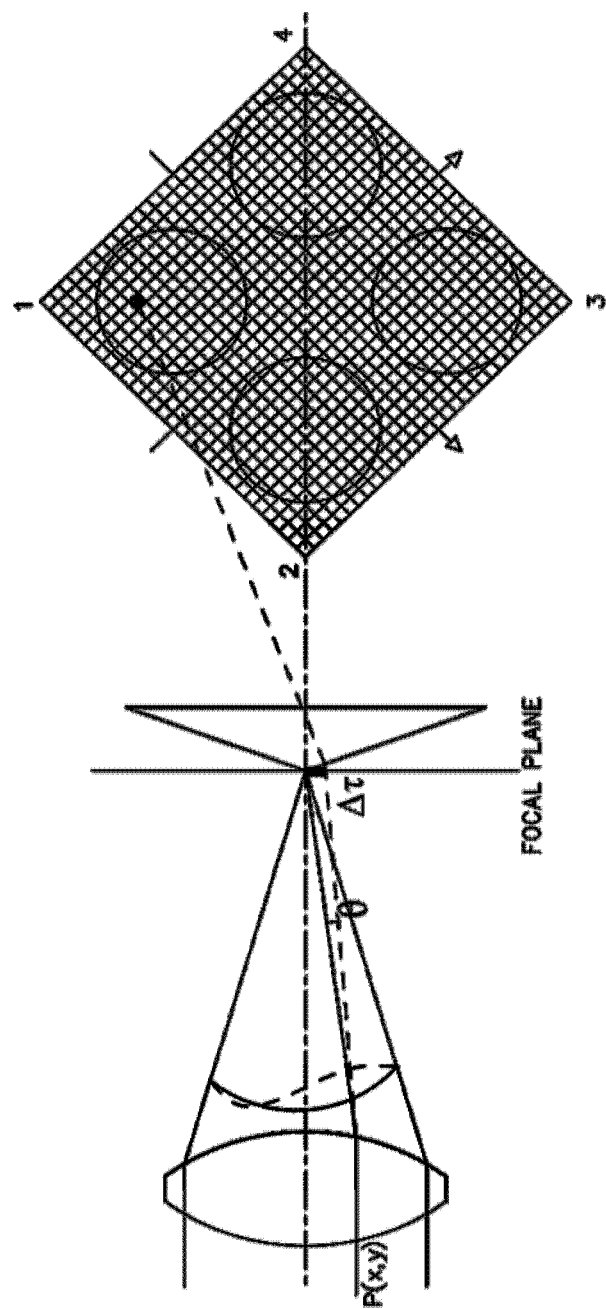
FIG. 3 schematically shows the operation of a PWS sensor.

A valid alternative to the HSS sensor borrowed from astronomy is the pyramid wavefront sensor (PWS). FIG. 3 schematically shows the operation of such a sensor.

This sensor, in geometric optics, is equivalent to two prisms positioned with perpendicular corners that generate four distinct images of the pupil (sub-pupil) on a sensor.

Calling the aberrated wavefront W and given the point P in the pupil of coordinates (x, y), it is possible to calculate the beam normal to W in P. Due to the aberration, such a beam will form an angle $\theta$ with the corresponding beam originating from W0 (spherical reference wavefront without aberrations): the aberrated beam on the focal plane will no longer hit the vertex of the pyramid, but at a distance $\Delta\tau$ from it. The angle $\theta$ is linked to $\Delta\tau$ by the relationship:

$$\theta = \Delta\tau/f$$

In turn $\theta$ is a measurement of the slope of the wavefront in a direction (for example y), hence:

$$\Delta\tau = f(\partial W(x,y))/\partial y$$

In practice, the displacement of $\Delta\tau$ of the point of incidence of the beam ensures that just one of the four sub-pupils is illuminated by the portion of the wavefront incident in P(x; y).

The unbalance of intensity in the regions of the four images of the pupil corresponding to P(x; y) contains the information on the slope of the wavefront incident at that point.

Figure 4:
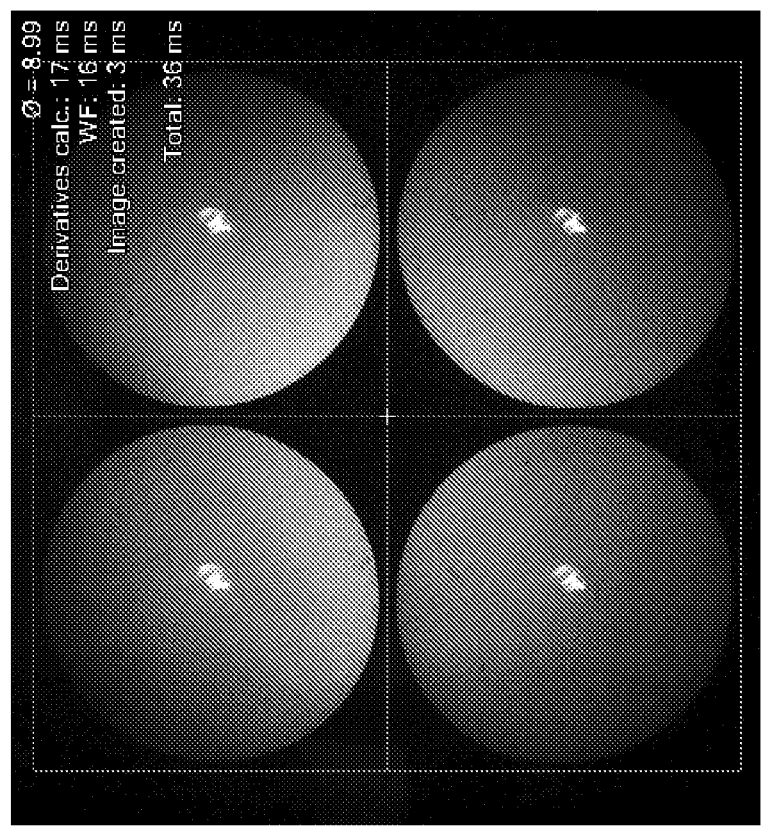
FIG. 4 is an example of sub-pupil images, obtainable through the PWS sensor.

FIG. 4 shows an output image of the four sub-pupils of an aberrometer with a PWS mounted.

Like the HSS, therefore, the PWS measures the slope of the wavefront, but, by sampling the wavefront on the sensor and upstream, for the same pupil, it has a number of samples that is about forty times greater than an HSS sensor, and therefore there is a much finer sampling pitch: this feature makes it particularly suitable for use with the present invention. It should be noted that the sampling pitch of the HSS cannot be reduced arbitrarily for diffraction reasons: in other words, if the size of the micro-lenses were reduced beyond a certain limit a diffraction would be introduced and therefore it would be impossible to estimate the aberrations.

The PWS was for the first time proposed by astronomers in order to measure the aberrations of the atmosphere as stated in the paper of R. Ragazzoni "Pupil plane wavefront sensing with an oscillating prism". The use of such a sensor in order to measure the human eye (combined or not with a closed feedback system consisting of adaptive optics) was proposed by Iglesias and Ragazzoni in WO2004025352. In this document there is explained how in the configuration indicated the entrance wavefront creates four images of the conjugated pupil on the CCD, the light intensity of which is dependent on the local variation of the wavefront itself.

The calculation technique proposed to derive the wavefront makes use of a best-fit method for the normals (or partial derivatives) of the wavefront with a set of Zernike polynomials.

In general, like in WO2004025352 (but see also as a further example CHAMOT ET AL: "Adaptive optics for ophthalmic applications using a pyramid wavefront sensor" OPTICS EXPRESS vol. 14, no. 2, 1 Jan. 2006, page 518), the classic wavefront reconstruction methods known in the literature are based on the search for a surface that best approximates the partial derivatives of the wavefront or in other words its normals. The common calculation procedure of the wavefront from the normals can be summarised in the following steps:

Selecting a set of base functions that are good describers of the surface to be represented, i.e. such that the wavefront can be expressed as a linear combination of these functions (series expansion) with a negligible residual error. There are various possibilities for the selection of these functions: the most common one in this field of application is the set of Zernike polynomials, but other families of functions that achieve the purpose should not be excluded.

Deriving each of the functions of the set, so as to obtain the analytical expression of the partial derivatives (normals).

Finding the set of coefficients of the series expansion that minimises the average quadratic error between the samples measured and the series expansion.

According to the present invention, on the other hand, a reconstruction method is proposed, preferably linked to an aberrometer that implements a PWS, based on the direct integration of the measured partial derivatives of the function representative of the wavefront.

Such a method is mathematically rooted in known numerical integration techniques of differential equations for example Euler, modified Euler, Runge-Kutta, etc.

In order to obtain an accurate reconstruction of the wavefront it is preferable to have samples of the partial derivatives measured very densely in the pupil: acceptable results are obtained with an inter-sample distance of less than 0.05 mm corresponding to about 7850 samples in a pupil of diameter 5 mm. This is a condition that is adequately fulfilled only in the case of use of a pyramid wavefront sensor (PWS). With no other sensor currently known in literature, especially not with the very widely used Hartmann Shack sensor where the measured samples are sparse and distant (the inter-sample distance of which is of the order of about 0.25 mm equal to about 1500 samples in a pupil of diameter 5 mm), would it be possible to successfully apply the method here proposed.

Figure 6:
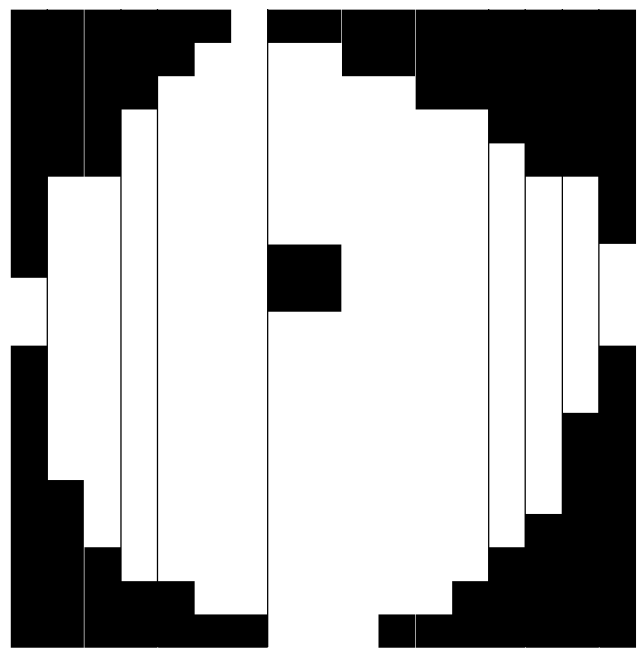
FIG. 6 represents a masking matrix M in which the black boxes correspond to opaque areas in the pupil.

For the extraction of the first order partial derivatives it is foreseen to process the images acquired, through image processing algorithms, to segment the images of the four sub-pupils and obtain a masking matrix M (shown as an example in FIG. 6) containing boolean values indicating whether or not there are completely opaque areas corresponding to the iris or to optical opacity.

From the four pupil images it is possible to obtain two matrices $\partial W/\partial x$ and $\partial W/\partial y$. They contain, where there are not opacities defined in the matrix M, the partial derivatives of the wavefront in the horizontal and vertical directions.

The procedure for extracting the matrices of the first order partial derivatives should be considered within the knowledge of a man skilled in the art and therefore will not be described here.

Direct Calculation of the Refracting Error Map

Such a map, in turn an aspect of the present invention, locally shows the difference in power of the eye examined with respect to the ideal. In particular, the farther the points of such a map are from zero, the more the defect will be accentuated. Therefore: myopic divergences will have a negative sign and hypermetropic divergences will show a positive sign.

The advantage of such a map is clear if one considers the fact that, while in the wavefront a simple refractive defect like a defocus is represented by a paraboloid, in the case of this map a defocus is a plane.

Figure 5:
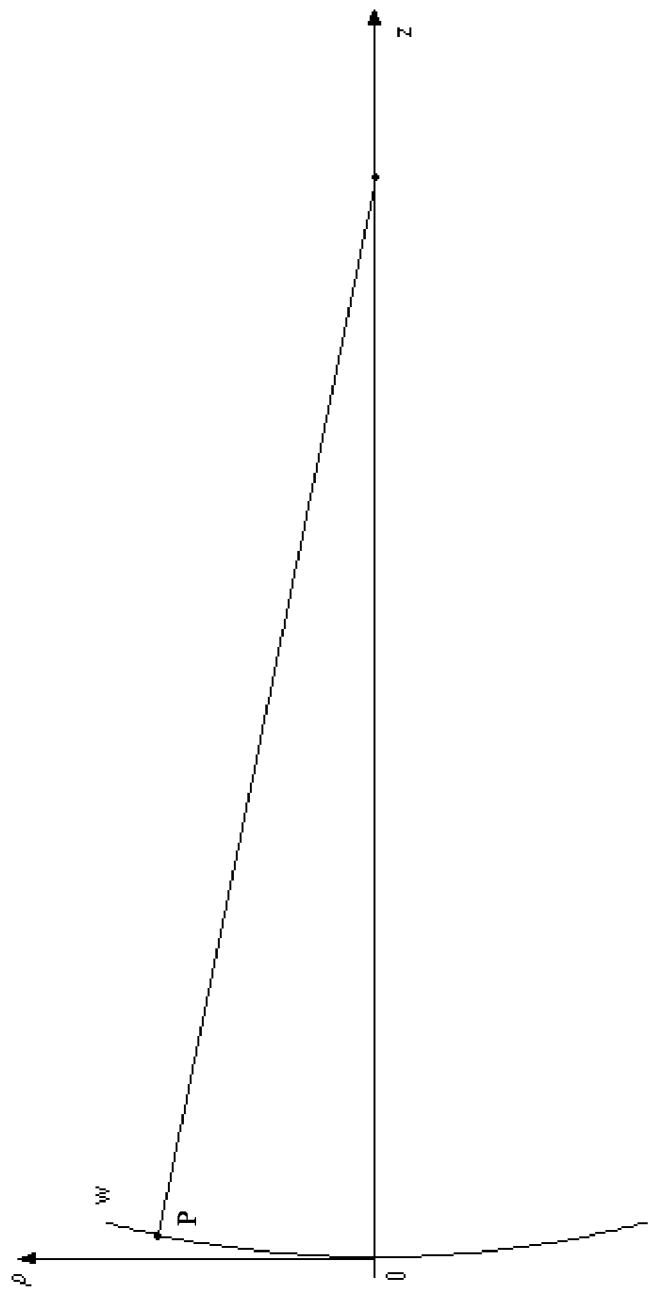
FIG. 5 is a schematization that can be used for calculating the refracting error.

With reference to the subsequent FIG. 5, being it said W the wavefront and given the point P in the pupil of coordinates (x, y) and its representation in polar coordinates (p, θ), to correctly evaluate the refractive defect it is necessary to know the direction of the normal to W in P and identify the point at which it intersects the visual axis z, as shown in FIG. 5. The inverse of the distance between this point and the origin defines the refractive defect for the corresponding point in the pupil and is expressed in dioptres ($m^{-1}$).

As can easily be understood from FIG. 5 the inverse of the refractive defect can be expressed as:

$$z = W + \frac{\rho}{\frac{\partial W}{\partial \rho}}$$

Given that z is of the order of millimeters whereas the wavefront is a few orders of magnitude lower, the formula can be simplified into:

$$z = \frac{\rho}{\frac{\partial W}{\partial \rho}}$$

and the refractive defect V into:

$$V = \frac{1}{\rho}\frac{\partial W}{\partial \rho}$$

which only depends on the derivatives of the wavefront.

The common calculation procedure of the refracting error map results from the calculation of the aforementioned wavefront. In particular, once the set of coefficients of the expansion that best represents the wavefront has been calculated, the refracting error is calculated as:

$$V = \frac{1}{\rho}\frac{\partial W}{\partial \rho} = \frac{1}{\rho}\frac{\partial \sum c_i Z_i(\rho, \vartheta)}{\partial \rho} = \frac{1}{\rho}\left(\sum c_i \frac{\partial Z_i(\rho, \vartheta)}{\partial \rho}\right)$$

where $c_i$ and $Z_i$ are, respectively, the i-th coefficient and the i-th Zernike polynomial. In the commonly used calculation procedure, therefore, the calculation of the refracting error map results from the calculation of the wavefront through fitting as indicated by J. Nam, L. N. Thibos, D. R. Iskander in "*Describing ocular aberrations with wavefront vergence maps*"

On the contrary, as already mentioned, the present invention proposes to reconstruct the wavefront from said first order partial derivatives and therefore the fitting procedure indicated by Nam et Alii will be avoided: the fact of having obtained the partial derivatives of the wavefront along the directions x and y, offers the possibility, therefore, of directly obtaining, without heavy processing, also a refractive defect map extending to the entire entrance pupil of the patient.

The advantages of this are massive, given that the possibility of a quick calculation of the equivalent defocus of the patient (obtained by averaging the refractive defect map) makes it possible to drive a mechanical optical system for compensation of the defocus with continuous feedback in order to maximise the dynamics of the wavefront sensor.

Indeed, it is possible to think of a particular configuration in which a slider induces a known amount of spherical defect in order to compensate that measured in the patient: this system, known as Badal, is well known to men skilled in the art.

Direct Calculation of the Wavefront Map

In particular, in the method according to the present invention after having calculated the partial derivatives of the wavefront by means of the sub-pupil images acquired, there comes next a direct integration of the aforementioned partial derivatives in order to obtain the wavefront.

As a preliminary assumption, it shall be considered that in general, if a series of points is given $(x_i, f(x_i))$ i=0, N−1 with $x_0 < x_1 < x_2 < x_3 < \ldots < x_{N-1}$ that are the first derivatives of f(x) calculated in $x_i$ of an unknown function f(x), and an initial condition $f(x_0)=c$, it is possible to determine the progression of f(x), in particular the value $f(x_i)$ of f(x) in $x_i$, by applying one of the known numerical integration methods in the literature (Euler, Runge-Kutta at the first order or at the order n, etc.).

Hereafter, as an example, use will be made of the Euler integration method. The other methods can be easily used as an alternative by a man skilled in the art:

Therefore, being it said $f(x_0)=c$, there results, for i=1, ..., N $f(x_{i+1})=f(x_i)+(x_{i+1}-x_i)*f'(x_i)$.

In the context of the present invention, in order to reconstruct the wavefront, the function W(x, y) that describes the wavefront has two independent variables x and y.

Figure 7:
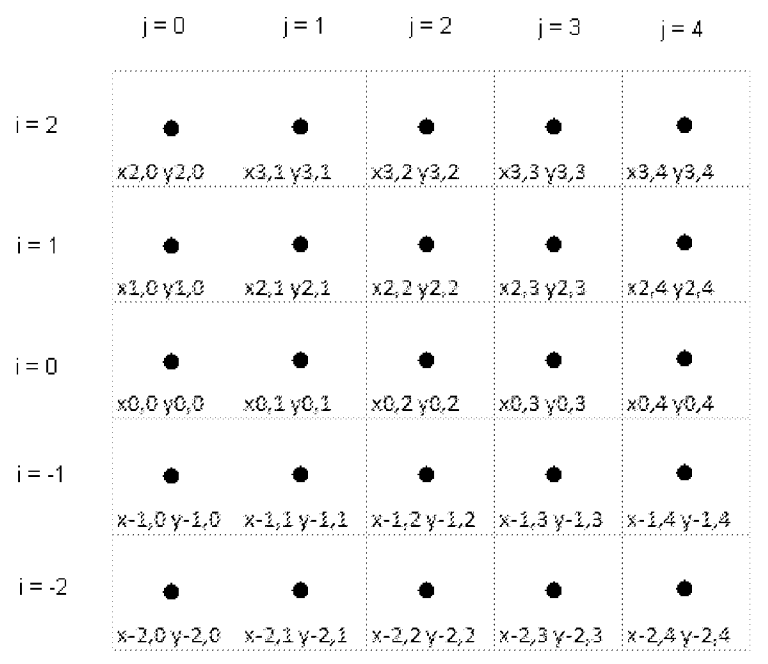

In the method according to the present invention the partial derivatives $\partial w/\partial x$ and $\partial w/\partial y$ in a series of points $(x_{i,j}, y_{i,j})$ in the pupil are calculated. FIG. 7 shows such a series of points, as an example.

In order to reconstruct W(x, y) in points $x_{i,j}$, $y_{i,j}$ it is possible to adopt the following strategy:

A starting point is set, i.e. i and j are set.

Assuming that:

RI is a numerical integration step towards the right characterised by the formula $W(x_{i,j+1}, y_{i,j})=W(x_{i,j})+(x_{i,j+1}-x_{i,j})*\partial w/\partial x (x_{i,j}, y_{i,j})$ LI is a numerical integration step towards the left characterised by the formula $w(x_{i,j-1}, y_{i,j})=W(x_{i,j})+(x_{i,j-1}-x_{i,j})*\partial w/\partial x (x_{i,j}, y_{i,j})$ UI is a numerical integration step upwards characterised by the formula $W(x_{i,j}, y_{i+1,j})=W(x_{i,j})+(x_{i+1,j}-x_{i,j})*\partial w/\partial x (x_{i,j}, y_{i,j})$ DI is a numerical integration step downwards characterised by the formula $W(x_{i,j}, y_{i-1,j})=W(x_{i,j})+(y_{i-1,j}-y_{i,j})*\partial w/\partial x (x_{i,j}, y_{i,j})$ One moves in the direction of the increasing x, so that there are points available to the right, using a formula of the RI type.

One moves in the direction of the decreasing x, so that there are points available to the left, using a formula of the LI type.

Once the reconstruction of the points $W(x_{i,j}, y_{i,j})$ of the row i for each j has ended, one starts with the reconstruction of each column j or rather, for each j, a formula of the UI type is applied that moves towards the top part of the grid, or of the DI type if moving towards the bottom part of the grid.

In the previous description it was chosen to reconstruct first one row and then all of the columns: another strategy of the algorithm can be that of reconstructing firstly one column and then all of the rows.

Figure 9:
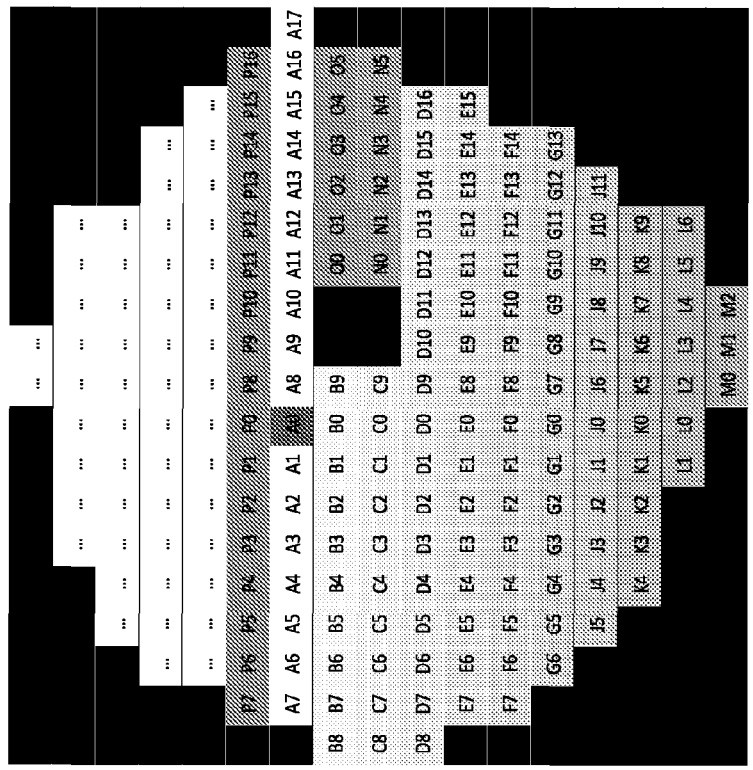
FIGS. 8 and 9 constitute a graphical representation of a possible algorithm according to the present invention, and FIG. 10 gives, as an example, a comparison between a reconstruction obtained with a prior art method and one obtained with a method according to the present invention.
Figure 8:
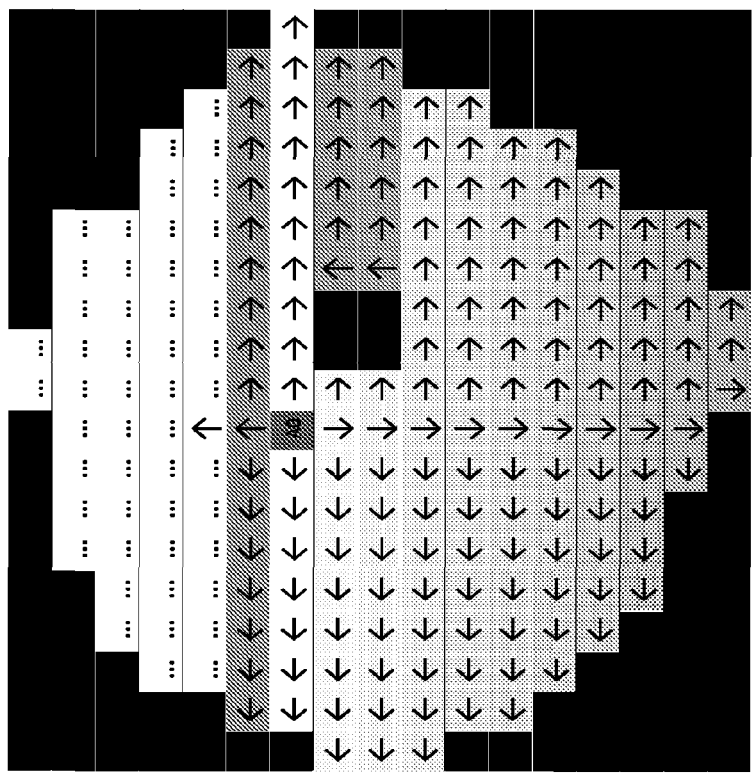

Reference is now made to FIGS. 8 and 9 that constitute a graphical representation of a possible algorithm according to the present invention.

In particular, from an algorithmic point of view it is possible to implement, for example through suitable software, a recursive function "WfReconstruct($x_0$, $y_0$, val)" the steps of which are described below:

a) If the element $M(x_0, y_0)$ of the matrix M indicates that $x_0, y_0$ is a valid point, then the fixed value val is assigned to $W(x_0, y_0)$.

b) The matrix is scrolled to the left applying the formula LI of the numeric integration until an invalid point is found on M. Each time a valid pixel is visited, the corresponding element of M is marked as invalid (because visited) in order to avoid an infinite recursion being triggered. The index of the last valid element in the row will be memorised and saved as Lx.

c) The matrix is scrolled to the right applying the formula RI of the numeric integration until an invalid point is found on M. Each time this operation is carried out the corresponding element of M is marked as invalid (because visited) in order to avoid an infinite recursion being triggered. The index of the last valid element in the row will be memorised and saved as Rx.

d) For each point $P(x, y_{0+1})$ with x between $x_0$ and Lx the recursive function from point a) is called upon again, giving as starting value the $W(x, y_0)$ found in points b or c.

e) For each point $P(x, y_{0-1})$ with x between $x_{0+1}$ and Rx the recursive function from point a) is called upon again, giving as starting value the $W(x, y_0)$ found in points b or c.

For example through a calculation algorithm of the centroid on the pupil image it is possible to identify a first point A0 from which to start. It is supposed that the selected point is a valid point in the matrix M.

The recursive function WfReconstruct is launched with the values $x_0 = x_{A0}$ and $y_0 = y_{A0}$ and val=0. This becomes the condition at the perimeter for the numeric integration and it is absolutely arbitrary given that it only has the effect of translating the wavefront and does not have consequences from the optical point of view.

Starting from point x, y of A0 one heads first to the left up to A7 [c], and then to the right up to A17 [d]. The first recursive call will be from point A0 downwards [d] and in turn it will fill row B up to the first invalid point. The algorithm will continue up to row M filling the bottom part of the pupil to then continue filling on row N and O launched, respectively, from D12 and N0. Once the row O is finished, all of the recursions will be ended by the fact that the matrix M is completely filled in the bottom part and it will go back to launch the recursion of point A0 in the top part [e]: this will allow the top part of the pupil to also be filled.

An alternative version of the algorithm can scan firstly the columns instead of the rows and carry out the recursion on the rows in an entirely analogous way to what is written above.

It is also possible to adopt a further method in which the two previous versions of the algorithm are carried out and then the reconstructed wavefronts are averaged to obtain more noise rejection.

Figure 10:
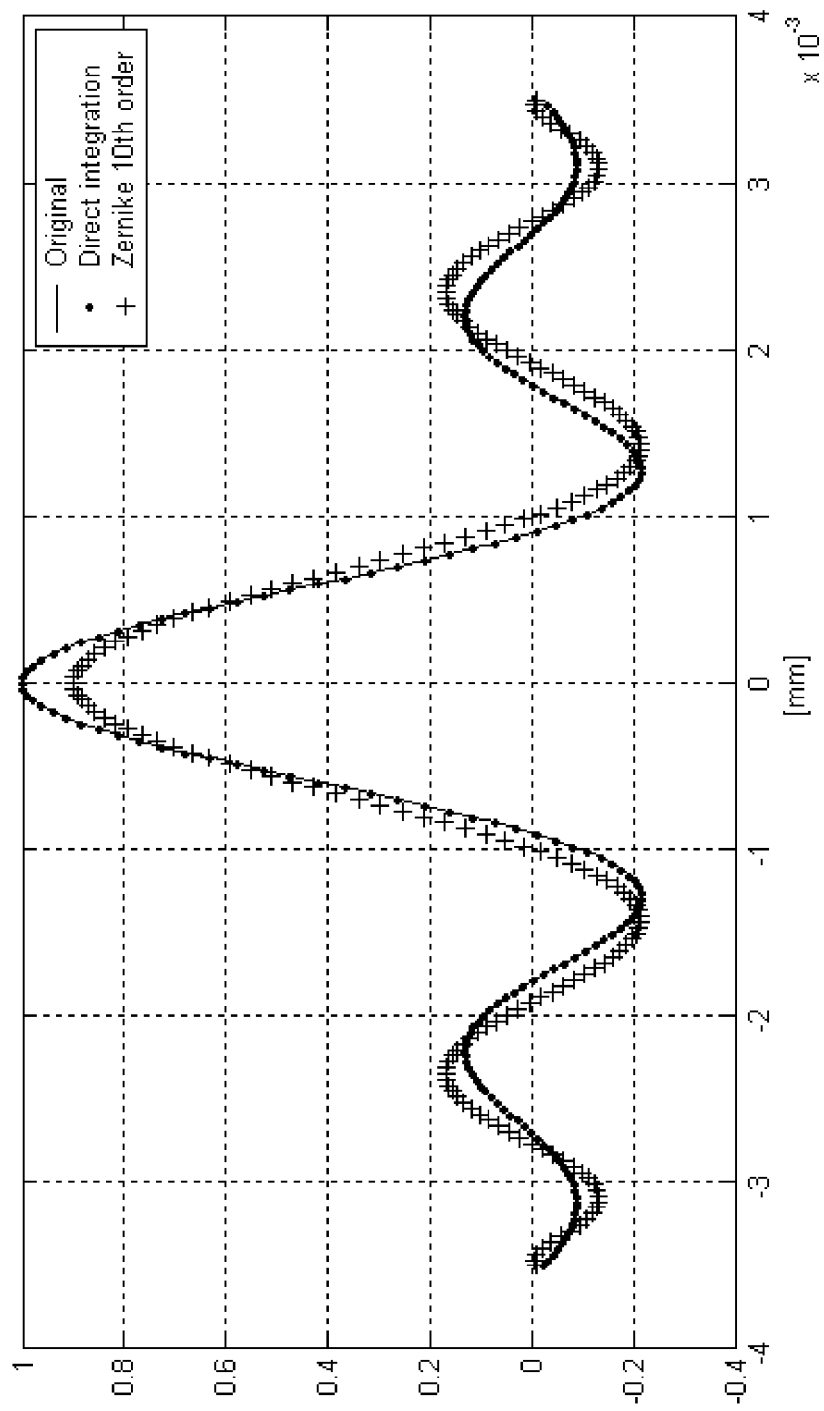

The subsequent FIG. 10 shows, again as an example, a comparison between a reconstruction obtained with a method of the prior art, in particular with a tenth order Zernike fitting, and with a method according to the present invention. As can be seen the reconstruction with the direct integration method manages to faithfully follow the progression of the function unlike the series of Zernike polynomials.

Again according to the present invention, it is thus possible to obtain an apparatus for measuring aberrations of an ocular optical system of a patient, which comprises means for lighting a retina of a patient, in particular a light source such as a laser or similar.

Moreover, the apparatus comprises means for detecting a light portion reflected by the retina, through a sensor comprising at least one prism adapted to split the pupil image in three or more sub-pupil images.

In particular, it is preferable for such a prism to be pyramid shaped and thus adapted to produce four sub-pupil images.

Such sub-pupil images can be acquired, preferably in digital format, through corresponding acquisition means. It does not appear necessary here to give a detailed description of such means, since they are certainly within the knowledge of a man skilled in the art.

The apparatus also comprises means for processing the acquired images.

In particular, such means for processing comprise a programmable processor, and corresponding calculation software, to obtain the first order partial derivatives of the wavefront generated by the ocular optical system.

The software, for which no specific implementation will of course be described in detail, can carry out each of the processing steps foreseen by the method according to the present invention and described above.

Moreover, the apparatus can be provided with interface means, for example monitor, printer, etc., for the graphical representation of the partial derivatives calculated.

Preferably, these can be represented in the form of a map of values, each of said values being representative of a local refractive power of the ocular optical system.

In order to carry out the steps of the method used for reconstructing the wavefront, the software can be adapted to implement a direct numeric integration algorithm of said partial derivatives, where the result of said integration constitutes a function representative of the wavefront. Such algorithms have been thoroughly described above.

The present invention has been described with reference to its preferred embodiments. It should be understood that each of the technical solutions implemented in the preferred embodiments described here as examples can advantageously be differently combined one another, to create other embodiments, which derive from the same inventive core and in any case all within the scope of protection of the claims here attached.

The invention claimed is:

1. Method for measuring aberrations of an ocular optical system, comprising the steps of:
    lighting a retina of a patient;
    detecting a light portion reflected by the retina, through a sensor comprising at least a prism adapted to split the pupil image in three or more sub-pupil images;
    acquiring said sub-pupil images;
    processing said acquired images so as to obtain first order partial derivatives of a wavefront generated by the ocular optical system; and
    reconstructing said wavefront through an algorithm for direct numeric integration of said partial derivatives, and/or of obtaining a map of values from said partial derivatives, each of said values being representative of a local refracting error of said ocular optical system,
    wherein W(z, ρ) is the wavefront, where z represents a visual axis of the ocular optical system and ρ represents a polar coordinate, and the local refracting error is calculated according to the following formula:

$$V = \frac{1}{\rho}\frac{\partial W}{\partial \rho}.$$

2. Method according to claim 1, wherein said prism is pyramid-shaped with a square base and adapted to produce four sub-pupil images.

3. Method according to claim 1, wherein said numeric integration algorithm is based on Euler's numeric integration method.

4. Method according to claim 1, wherein said numeric integration algorithm is recursive.

5. Apparatus for measuring aberrations of an ocular optical system, comprising:
    means for lighting a retina of a patient;
    means for detecting a light portion reflected by the retina, through a sensor comprising at least a prism adapted to split the pupil image in three or more sub-pupil images;
    means for acquiring said sub-pupil images;
    means for processing said acquired images for obtaining first order partial derivatives of a wavefront generated by the ocular optical system; and
    software means for applying a direct numeric integration algorithm to said partial derivatives, the result of said integration being a function representative of said wavefront, and/or for calculating a map of values from said partial derivatives, each of said values being representative of a local refracting error of said ocular optical system,
    wherein W(z, ρ) is the wavefront, where z represents a visual axis of the ocular optical system and ρ represents a polar coordinate, and the local refracting error is calculated according to the following formula:

$$V = \frac{1}{\rho}\frac{\partial W}{\partial \rho}.$$

6. Apparatus according to claim 5, wherein said prism is pyramid-shaped with a square base and adapted to produce four sub-pupil images.

7. Apparatus according to claim 5, wherein said numeric integration algorithm is based on Euler's numeric integration method.

8. Apparatus according to claim 5, wherein said numeric integration algorithm is recursive.

9. Apparatus according to claim 5, wherein a mechanical optical system for compensating a defocus of the patient is driven in feedback by the refracting error data.

* * * * *